United States Patent
Thong

(10) Patent No.: US 7,076,299 B2
(45) Date of Patent: Jul. 11, 2006

(54) METHOD AND APPARATUS FOR PREVENTING HEART TACHYARRHYTHMIA

(76) Inventor: Tran Thong, 12491 NW. Woodland Ct., Portland, OR (US) 97229

( * ) Notice: Subject to any disclaimer, the term of this patent is extended or adjusted under 35 U.S.C. 154(b) by 561 days.

(21) Appl. No.: 10/396,138

(22) Filed: Mar. 24, 2003

(65) Prior Publication Data

US 2003/0187479 A1    Oct. 2, 2003

Related U.S. Application Data

(60) Provisional application No. 60/367,860, filed on Mar. 28, 2002.

(51) Int. Cl.
*A61B 5/0452* (2006.01)
(52) U.S. Cl. .......................... 607/14; 600/515
(58) Field of Classification Search ................ 600/515, 600/518; 607/3, 14
See application file for complete search history.

(56) References Cited

U.S. PATENT DOCUMENTS

| | | |
|---|---|---|
| 5,425,749 A | 6/1995 | Adams |
| 6,035,233 A | 3/2000 | Schroeppel et al. |
| 6,115,627 A | 9/2000 | Street |
| 6,161,041 A | 12/2000 | Stoop et al. |
| 6,205,357 B1 | 3/2001 | Ideker et al. |
| 6,272,377 B1 | 8/2001 | Sweeney et al. |
| 6,308,094 B1 | 10/2001 | Shusterman et al. |
| 6,370,431 B1 | 4/2002 | Stoop et al. |
| 6,400,982 B1 | 6/2002 | Sweeney et al. |
| 2002/0016550 A1* | 2/2002 | Sweeney et al. ............ 600/515 |

* cited by examiner

*Primary Examiner*—Robert Pezzuto
*Assistant Examiner*—Yun Haeng Lee

(57) ABSTRACT

The invention is for a method for predicting an imminent episode of ventricular tachyarrhythmia by an analysis of the variations in the heart beat frequency during otherwise normal appearing sinus rhythm in the normal beat frequency range. The analysis is based on detecting a prolonged pattern of increasing heart beat rate. When the method is implemented by hardware it can initiate, or cause to be initiated, preventive therapies. A further implementation can cause the patient or attendant to be notified of imminent ventricular tachyarrhythmia. Both implantable and external devices are considered.

24 Claims, 6 Drawing Sheets

METHOD AND APPARATUS FOR PREVENTING HEART TACHYARRHYTHMIA

CROSS-REFERENCE TO RELATED APPLICATIONS

This application claims priority and other benefits from U.S. Provisional Patent Application Ser. No. 60/367,860, filed Mar. 28, 2002, entitled "PREVENTION OF HEART TACHY ARRHYTHMIA".

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISK APPENDIX

Not Applicable

BACKGROUND OF THE INVENTION a. Field of the Invention

The present invention relates to a method for predicting an imminent episode of ventricular tachyarrhythmia, namely ventricular tachycardia and ventricular fibrillation, based on a rhythm acceleration pattern, and the associated preventive/warning implantable cardiac devices and preventive/warning external cardiac monitoring devices.

b. Description of Prior Art

Currently there is no effective device for predicting, and then preventing, an imminent episode of life threatening ventricular tachyarrhythmia (VTA), namely ventricular tachycardia, which often accelerates into a lethal ventricular fibrillation. Drug therapies can be used, but these anti-arrhythmic drugs typically have undesirable side effects. Clinical experience has shown that at acceptable level, these anti-arrhythmic drugs can reduce but not eliminate completely episodes of VTA. An effective device for treating, as opposed to preventing, ventricular tachyarrhythmia is the implantable cardioverter defibrillator (ICD). An ICD is implanted in a patient at risk of sudden cardiac death, caused by an episode of VTA. However, the ICD can treat, but cannot prevent these episodes of VTA.

In prior art, a number of systems for predicting ventricular tachyarrhythmia have been proposed.

In U.S. Pat. No. 5,425,749 to Adams, et al., issued Jun. 20, 1995, we are taught about a method to give a preemptive shock when an episode of VTA is predicted. One method for prediction is based on detecting a burst of high rate events, typically 3 beats at 200 beats per minute. An alternate prediction uses the "slope filtered pointwise correlation dimension algorithm" which is based on chaos theory measurement of the correlation between samples of R-R intervals. In the applicant's own experience, the first method of prediction is only predictive of a small number of episodes of VTA. The amount of computation involved in the second method for prediction is not easily implemented either in an implantable device or in a bedside monitor.

In U.S. Pat. No. 6,035,233 to Schroeppel, et al., issued Mar. 7, 2000, we are taught about a system that monitors heart rate variability measures such as mean atrial rate, mean absolute deviation, activity, and respiration. A set of normal and abnormal templates are stored. When the measurement changes away from the normal templates towards an abnormal template, a prediction of imminent tachyarrhythmia is made. None of the literature since the filing of this patent has validated the concept of using such templates.

In U.S. Pat. No. 6,058,328 to Levine, et al., issued May 2, 2000, we are taught about preventive pacing to prevent an episode of VTA. The method for triggering this preventive pacing is the deviation of the heart rhythm from a template which can be made adaptive to take into account the history of heart rhythm prior to recorded episodes of VTA. It should be noted that a slow rhythm acceleration would not be considered a marker for VTA for a person skilled in the art at the time of the issue of this patent. Such a rhythm has been considered indicative of a sinus tachycardia in response to increased metabolic demand.

In U.S. Pat. No. 6,115,627 to Street, issued Sep. 5, 2000, we are taught to use the power spectrum to predict an imminent episode of tachyarrhythmia. This is related to the extensive work in the literature on heart rate variability. While it has been recognized that a depressed high frequency (>0.15 Hz) spectrum is a marker for ventricular tachyarrhythmia due to reduced parasympathetic cardiac control, the use of this marker as a predictor of an imminent episode of ventricular tachyarrhythmia has not been documented in the literature since the filing of this patent.

In U.S. Pat. No. 6,161,041 to Stoop, et al., issued Dec. 12, 2000, we are taught about a pacemaker with overdrive pacing to prevent episodes of VTA. The trigger for the overdrive pacing is deviation from stored templates of the QRS and T waveforms, or a coupling time from a QRS complex to a ventricular premature complex that would result in the premature complex occurring during repolarization, i.e. during a T wave. To support these triggers the pacemaker must use non standard sensing circuits since most pacemakers are designed with filters that attenuate T waves.

In U.S. Pat. No. 6,205,357 to Ideker, et al., issued Mar. 20, 2001, we are taught about a system that uses a multitude of electrodes to determine the site of ectopic beats and then deliver preventive therapies in the form of isolated pacing pulses. However, it is well known from the Cardiac Arrhythmia Suppression Trials (Myerburg, et al., "Interpretation of Outcomes of antiarrhythmic clinical trials, Circulation, 1998;97: 1514–1521) that premature (ectopic) beats are not well correlated with sudden cardiac death risk because they happen too often. Thus, the predictor in this system is likely to exhibit a high false positive rate resulting in frequent unnecessary interventions, which themselves may initiate a life threatening ventricular tachyarrhythmia. While these episodes can be terminated by the device, they increase the risk of death by electromechanical dissociation, that may follow an episode of device-terminated ventricular tachyarrhythmia (Mitchell, et al., "Sudden death in patients with implantable cardioverter defibrillators: the importance of post-shock electromechanical dissociation", J Am Coll Cardiology, 2002:39: 1323–1328).

In U.S. Pat. No. 6,272,377 to Sweeney, et al., issued Aug. 7, 2001, and further refined in U.S. Pat. No. 6,400,982 to Sweeney, et al., issued Jun. 4, 2002, and U.S. Patent Application US 2002/0016550 to Sweeney, et al., published Feb. 7, 2002, we are taught that the implanted device can monitor for marker and trigger conditioning events of ventricular tachyarrhythmia and provide a multitude of preventive therapies including pacing. Example of conditioning events considered are: waveform morphology, specific pattern of activation times of different areas of the heart using a multitude of electrodes in the heart, specific pattern of heart beats with respect to time, heart rate, blood pressure. When a plurality of such conditioning events occurs, the probability of an arrhythmia is calculated and appropriate preventive therapy can be initiated. It should be again noted that a slow cardiac rhythm acceleration would not be considered a marker for VTA for a person skilled in the art at the time of the issue of these Sweeney's patents, or publication of the Sweeney's patent application. Such an acceleration has been considered indicative of a sinus tachycardia in response to increased metabolic demand.

In U.S. Pat. No. 6,308,904 to Shusterman, et al., issued Oct. 23, 2001, we are taught about a system that uses Karhunen Loeve Transformations on the heart rhythm, namely the R-R series, for predicting the occurrences of cardiac arrhythmia from one to three hours prior to the episode of VTA. The computational requirement required for such a system is beyond what can be implemented in an implantable device. Even in a bedside monitoring device, the computational requirement would make this impractical.

In U.S. Pat. No. 6,370,431 to Stoop, et al., issued Apr. 9, 2002, which is a continuation of U.S. Pat. No. 6,161,041 cited above, we are taught to monitor the QT interval and the rate of ventricular extra systoles to predict an imminent episode of VTA. When a prediction of imminent VTA is made, overdrive pacing is initiated. Again, the issue here is that special sensing circuits are needed to detect T waves, which are normally attenuated in conventional pacemakers and ICDs. The rate of ventricular extra systoles has not been found in numerous studies to correlate well with imminent episodes of VTA.

In the ventricular tachyarrhythmia prediction literature, two approaches have been proposed.

Skinner, et al. (Skinner, et al., "A reduction in the correlation dimension of heartbeat intervals preceded imminent ventricular fibrillation in human subjects", Am. Heart J., 1993:125: 731–743) have proposed a predictor based on a chaos-based measurement. The correlation dimension is the $\log_r$ (log based r) of the fraction of the total number of heartbeat intervals analyzed within a small radius, r. This type of measurement must be done retrospectively since all the data must be available for analysis. Thus, it cannot be used in real-time to predict an imminent episode of VTA. Note that this algorithm is a more general version of the "slope filtered pointwise correlation dimension algorithm" of U.S. Pat. No. 5,425,749 to Adams cited above.

Mäkikallio, et al. (Mäkikallio, et al., "Heart rate dynamics before spontaneous onset of ventricular fibrillation in patients with healed myocardial infarcts", Am J Cardiol, 1999:83: 880 884) used a different chaos-based measurement to predict an imminent episode of tachyarrhythmia. The root-mean-square of the deviation of the heart beat intervals, collected over hours, is analyzed using different window lengths. The slope of the deviations over these windows is computed. It was observed that this slope decreases prior to an episode of VTA. The length of data needed to perform a reliable analysis and the complexity of the computation preclude the implementation of this method in a real-time device.

What is needed is a simple and reliable method for predicting an imminent episode of ventricular tachyarrhythmia. Simplicity is needed for implementation in a cardiac device, either an implantable device or a bedside monitor. Simplicity also means that it is easy to adjust to the particular conditions of the patient. In the prior art no simple and reliable method has been described. Furthermore in all the methods described, a prolonged heart rate acceleration, while the rate remains within the accepted normal range of less than 120 beats per minute, would not be considered a marker for ventricular tachyarrhythmia. Such an acceleration would have been considered a normal sinus tachycardia.

BRIEF SUMMARY OF THE INVENTION

The application is about a method for processing the heart beat intervals, the R-R intervals, to predict an imminent episode of ventricular tachyarrhythmia (VTA) and the action or actions to be taken by a cardiac device with the prediction method built in, when a prediction of imminent VTA is made. This invention does not depend on the particular method for measuring the R-R intervals, as long as it can be done reliably. While this application uses the electrocardiogram to illustrate how R-R intervals can be measured, it is equally applicable when other methods for measuring R-R intervals are used, for example in a pulse oximeter, or a continuous blood pressure measuring device.

The invention is described in this application in terms of R-R intervals. This invention is equally applicable when heart rate, which is the reciprocal of the R-R interval, is used.

In this application the words cardiac and heart are used interchangeably.

All commercially available ICDs have a built-in pacemaker. Thus, in this application any reference to an ICD assumes a pacemaker capability for sensing intracardiac electrogram and pacing to treat bradycardia. In addition to the pacemaker functions, an ICD also has the capability to detect ventricular tachycardia and ventricular fibrillation and to provide the appropriate pacing and shock therapies. On the other hand, any explicit reference to a pacemaker precludes the capability to deliver shock therapy, but assumes the capability to provide all the pacing therapies available in an ICD, including high rate pacing. This is within the capabilities of commercial pacemakers with the appropriate program.

A VTA is characterized by a high heart rate, typically greater than 120 beats per minute, not associated with an increased metabolic demand. Increased heart rate in response to increased metabolic demand such as during physical or mental exertions, is considered normal sinus tachycardia. One criterion that has been used in ICDs to differentiate between VTA and sinus tachycardia has been the rate of change of the heart rate. A VTA is associated with a rapid onset, typically the rate increases to over 120 beats per minute in just a few beats. A normal sinus tachycardia takes 10–20 beats to reach its high rate, which may or may not be faster than 120 beats per minute, typically taken as the lower limit of VTA, specifically of ventricular tachycardia.

In this application, an imminent episode of VTA is defined to be one that will occur within 15 seconds to two hours. With a prediction time of less than 15 seconds, there may currently be insufficient time to initiate any effective preventive action, and thus this is not useful. If the prediction time is greater than two hours, it is questionable whether any preventive action, as described in this submission, would have lasting effect. These time limits are based on the current state of therapy technology. They will change as therapy technology, be it electrical- or mechanical- or drug-based, improves. However the methodology as described herein will endure. Only these 15 seconds and 2 hour time limits may be altered.

The invention stems from the unique observation that there is a direct correlation between a specific R-R interval pattern and the imminent onset of VTA. The explanation of why this correlation exists is based on the hypothesis that an episode of VTA can occur only due to a temporary depression of the parasympathetic (vagal) nervous system. Vagal activities act to slow the cardiac rhythm whenever the rate of cardiac depolarization, which under normal circumstances generate the heart beats, speeds up due to causes other than increased metabolic demand. Generally speaking, left on its own, without vagal intervention "putting on the brakes", these rapid cardiac depolarizations will cause an episode of VTA. The temporary depression of the vagal control activities has been labeled in this application as "vagal fatigue". The present invention uses the information contained in the R-R intervals to predict an imminent episode of VTA. A specific pattern of these R-R intervals occurs during sinus rhythm, while the heart rate is within its normal range. From analyses of stored R-R interval history of ICD patients, recorded prior to episodes of VTA, the applicant found that the best predictor of an imminent VTA is a prolonged rhythm acceleration. This rhythm acceleration, which is a progressive shortening of the R-R intervals, lasts more than 30 seconds, which generally corresponds to 40–60 heart beats. Note that this acceleration takes longer than the onset of a normal sinus tachycardia, which takes typically 10–20 beats, as indicated in earlier. During this time the R-R intervals remain longer than 500 milliseconds, corresponding to heart rhythms slower than 120 beats per minute.

The key difference between the method for predicting an imminent episode of VTA of the present invention from the prior art is the use of this prolonged cardiac rhythm acceleration. In the prior art, such an acceleration would have been considered a benign sinus tachycardia in response to increased metabolic demand. Except for the increased duration, it would be similarly considered in this invention.

This rhythm acceleration pattern can be found by the following method.

The R-R intervals during normal sinus rhythm are monitored continually. The long term R-R interval average is calculated over the past 10–30 seconds. The current R-R interval is compared to the above mentioned long term average (LTA). The duration of time that the current R-R interval remains shorter than the LTA is computed. In the preferred embodiment, the duration is counted in R-R intervals. An alternative would be to measure the time in units of milliseconds. As an example consider the following sequence of pairs of R-R interval followed by the LTA, all specified in units of milliseconds: (900, 900), . . . , (900, 900), (870, 899), (840, 896), (810, 891), (780, 885), (750, 878), (900, 878). The LTA, which is continually updated, is computed in this example from the last 20 R-R samples. In this example the rhythm acceleration has lasted 5 R-R intervals and ended with the pair (900, 878), because the current R-R interval has become larger than the LTA. If the duration of such a pattern of ever decreasing R-R intervals exceeds a prescribed duration criteria, such as 60 R-R intervals, a vagal fatigue warning is issued, which is the prediction that an episode of VTA is imminent.

Descriptions of the proposed method of R-R analysis have been published: Thong (the applicant), Goldstein, "Prediction of tachyarrhythmia episodes", Proceedings of the Second Joint IEEE EMBS/BMES Conference, Houston, Tex., Oct. 23–26, 2002, pp. 1445–1446; Thong (the applicant), Goldstein, "Prediction of ventricular tachyarrhythmia episodes from heart rhythm data by a vagal fatigue index", American Heart Association 2002 Scientific Sessions, Chicago, Ill., Nov. 17–19, 2002, Abstract 435, Circulation, Vol. 106, No. 19, p. II-86.

The applicant found the sensitivity for the vagal fatigue predictor to be in excess of 50% for the 247 episodes of tachyarrhythmia analyzed. Excluding episodes of tachyarrhythmia that self-terminated prior to therapy, and for which the vagal fatigue predictor was not found, the latest results indicate a sensitivity in excess of 80%, making the vagal fatigue predictor a reliable predictor of imminent episodes of ventricular tachyarrhythmia.

When an implementation of this vagal fatigue warning is incorporated in a new type of preventive ICD, it can be used to trigger a preventive pacing therapy. During this preventive therapy the heart is paced at an elevated rate, for example 10 to 15 beats per minute faster than the current LTA but less than a limit, programmable by the physician but expected to be about 120 beats per minute. This increased pacing rate would continue for a duration from a few minutes to a couple of hours, as programmed by the physician. The benefit of this elevated pacing therapy is to improve cardiac blood perfusion thereby strengthening the heart. Another benefit of the elevated pacing therapy is a reduction of refractory dispersion, inhibiting the establishment of re-entry circuits responsible for most VTAs. Long term elevated pacing for many hours is not used to avoid a loss of effectiveness due to the heart adapting to this elevated pacing rate.

The vagal fatigue warning in the preventive ICD can also be used to signal the patient of the imminent episode of VTA either through an audio or vibrational signal. When the patient detects such a signal, he/she may take preventive actions, such as, but not limited to, taking an additional anti-arrhythmic drug dose, or make change in his/her behavior, such as resting or stopping an unhealthy behavior, e.g. anger. The warning can also be conveyed by wireless means to an external device worn by the patient that can convey the warning to a service center through cell phone like circuits. The service center, based on the history of the patient and the transmission that typically includes a short history of the patient's cardiac rhythm, may decide to alert the patient by phone or other means, and/or his/her cardiologist for recommendation on a plan of action.

The above vagal fatigue method for predicting an imminent episode of VTA can also be implemented in a new type of preventive pacemaker for patients with non-sustained and non-lethal VTA, i.e. ventricular tachycardia, that negatively affect their quality of life. While pacing therapy to terminate the VTA once it developed will not be attempted, due to concerns that the pacing therapy may accelerate the ventricular tachycardia into lethal fibrillation, preventive pacing therapy and/or warning can be programmed by the physician.

In a conventional ICD the episode of ventricular fibrillation is normally treated with shock therapy. After the fibrillation is detected, capacitors in the ICD are charged to the programmed energy, and then the shock is delivered. The shock is aborted at any time during the charging of the capacitors, which may take as long as 10 seconds, if the fibrillation self terminates prior to shock delivery. Any charge on the capacitors in an aborted shock is allowed to leak and consequently the charge energy is lost. In the case of the preventive ICD of this invention, in addition to the actions taken when a vagal fatigue warning is issued, when no prior vagal fatigue warning has been issued during a programmed time interval, e.g. 3 hours, or any other time related measurement such as heart beat count, a modification of the conventional ICD behavior can be programmed for the next time the ICD detects an episode of ventricular fibrillation. In the preventive ICD of this invention, the start of charging can be delayed by a programmable duration, for example 2–5 seconds, to allow the fibrillation an opportunity to self-terminate. If during the wait of 2–5 seconds, the fibrillation terminates on its own, the ICD would have saved at least a partial charge cycle and thus battery longevity would be extended. This delay may also save the patient from a painful shock if during the charging time the fibrillation self terminates. In this later case, there may be no battery charge saving though. The applicant, in his study of patient records, has found that up to 5 times more non-sustained episodes of ventricular fibrillation corresponded to no vagal fatigue indication over a prolonged period of time approaching hours, as episodes of sustained ventricular fibrillation without vagal fatigue detected. A similar delay strategy may also apply to ventricular tachycardia in patients with a high risk of arrhythmia acceleration due to ventricular tachycardia pacing therapy.

Instead of delaying therapy, the VTA detection parameters for the preventive implantable device can be altered to cause a similar effect. For example therapy is normally initiated upon counting 12 fast R-R intervals. Increasing the required count to 18 fast R-R intervals effectively delay therapy by 6 R-R intervals, which amounts to a delay of 2 to 3 seconds, depending on the values of the R-R intervals.

While the discussion in this application has focused on electrical therapy in implantable cardiac devices, this does not preclude the use of the method of the present application with drug therapy in a future implantable device.

When this vagal fatigue alarm is incorporated in an external device, generically a cardiac monitor commonly found in hospitals, which can for example be an electrocardiogram monitor or a pulse oximeter with heart rate measurement, the device can either generate an audible or electronic notification to inform the nurse of the condition, and/or initiate preventive action through another device, such as a mechanical drug pump. In the case of the alarm for the nurse, the nurse can increase the dose of anti-arrhythmic drug. Similarly for the drug pump.

DETAILED DESCRIPTION OF THE DRAWINGS

Figure 1:
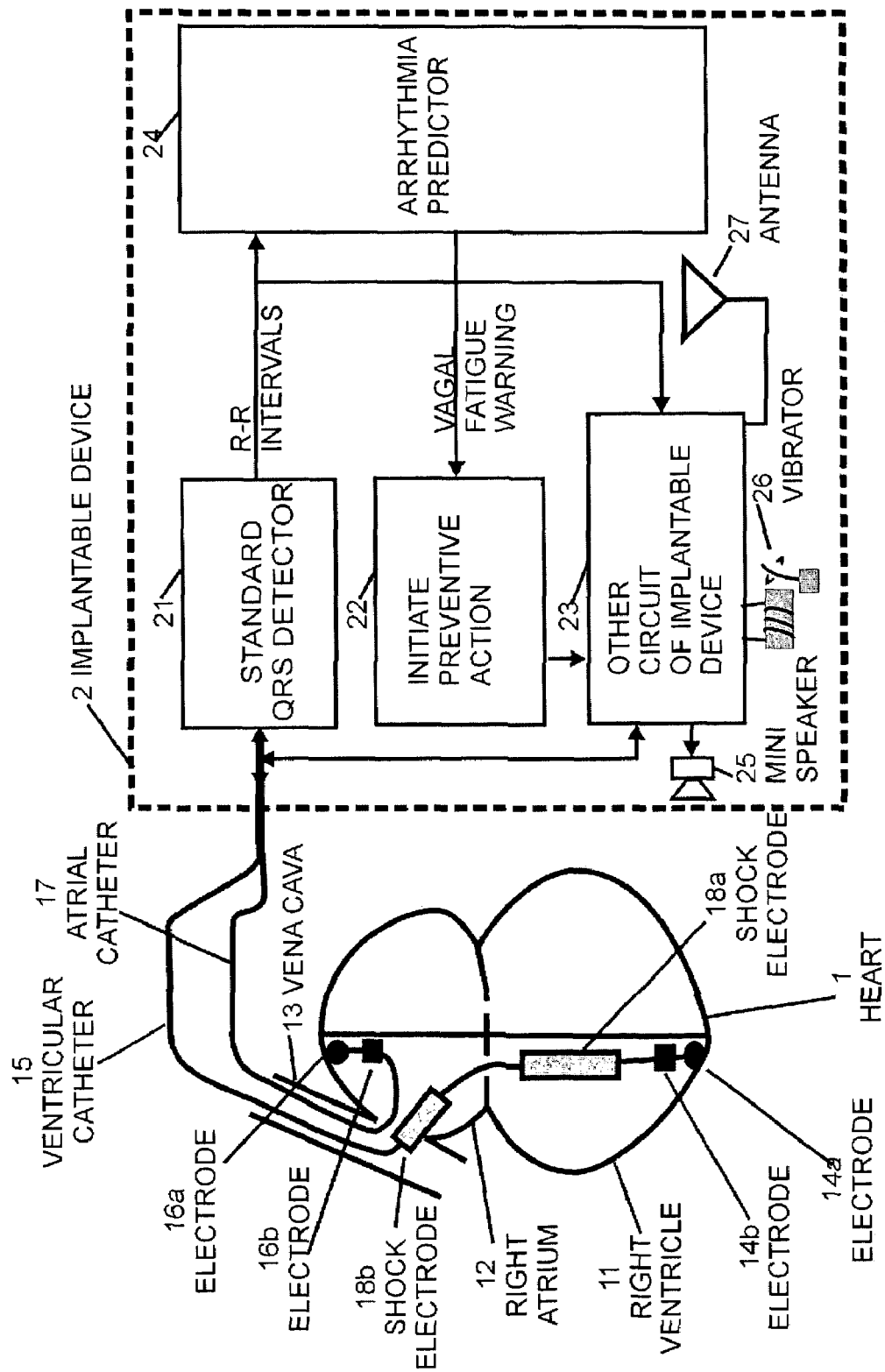
FIG. 1. is a functional schematic diagram of a preventive therapy implantable device according to a preferred embodiment of the present invention.

FIG. 1 shows the Heart 1 of the patient. The Right Ventricle 11, Right Atrium 12, and Vena Cava 13 are identified. Depending on the particular implantable device being used, one or more electrodes, which are located on a catheter introduced through a vein to reach the heart, are used. In the preferred embodiment two electrodes, 14a and 14b, located in the right ventricle and connected to the implantable device 2 on a single catheter 15, are used. Typically, the tip electrode 14a is positioned at the apex of the right ventricle, the ring electrode 14b floats in the ventricular blood pool, and the ventricular catheter 15 is introduced from a vein in the neck or shoulder area through the vena cava 13 and the right atrium 12 to reach the right ventricle 11. Also shown are the atrial electrodes 16a and 16b on the atrial catheter 17. This does not preclude the use of alternate methods of approach for the catheter and alternate locations for the electrodes. Additional electrodes, with additional catheters, can also be used to monitor or/and pace the other chambers of the heart, such as outside of the left atrium and left ventricle. Any of these catheters may carry a plurality electrodes, such as pace/sense electrodes, such as 14a, 14b, 16a, 16b, or shock electrodes, such as 18a and 18b.

The Implantable Device, 2, can be either an implantable cardioverter defibrillator (ICD) or a pacemaker. The ICD incorporates all the functionalities of a pacemaker and has the additional capability to deliver electrical energy therapies to terminate an episode of ventricular tachyarrhythmia, either by rapid pacing or by shock. The preferred device of the present invention is an ICD, but the invention would also apply to a pacemaker.

The intracardiac electrogram from the ventricular electrodes is fed to a standard QRS Detector, 21. For simplicity, standard signal conditioning circuitry commonly found with standard QRS detectors has not been explicitly shown, but is assumed. A typical QRS detector would have an analog threshold circuit. When the threshold is crossed, a count is started, typically in units of 4 or 8 milliseconds. The threshold circuit is refractory for some programmed time, typically 100 milliseconds, to avoid multiple detection of a single QRS complex. This count is reset at the next threshold crossing. The count corresponds to an R-R interval, which is provided as the digital output of the QRS detector. This is fed to the unique Arrhythmia Predictor, 24, of the present invention.

Since the method of the present invention operates on the R-R intervals during normal sinus rhythm, a substitute for the R-R interval is the P-P interval measured from the electrodes 16a and 16b in the right atrium 12 as illustrated in FIG. 1. In sinus rhythm, every QRS complex is preceded by a P wave. In intracardiac measurements, the magnitude of the P wave is large enough that it can be sensed reliably in most patients. A P wave detector would be functionally identical to a QRS detector. As indicated, use of the P-P interval is not the preferred embodiment of this invention, but could be used as an alternate embodiment should the R-R intervals not be available for implementation of the present invention. In such a system, ventricular electrodes would still be required to detect the episodes of VTA.

A further alternate method to measure R-R intervals is to make far field measurements. An ICD is implanted with pace/sense electrodes as indicated in FIG. 1, and additional ventricular shock electrode 18a, and possibly in the atrium or vena cava, such as 18b. The housing of the device 2 may also act as a shock electrode. In this case, the signals sensed from the ventricular shock coil 18a are combined with the signals from either another shock coil 18b in the atrium or vena cava, and/or with the housing of the implantable device 2. The resulting signal, with a large QRS complex, is similar to that obtained from a surface electrocardiogram. The QRS detector in this case would be very similar to the unit 21 shown in FIG. 1.

Using the method described below, the Arrhythmia Predictor issues a Vagal Fatigue Warning when an imminent episode of ventricular tachyarrhythmia is detected. This warning is acted upon by the Initiate Preventive Therapy, 22, which causes action to be taken by the implantable device through block 23 that represents other circuits commonly found in implantable devices. For example a preventive pacing regimen is initiated that lasts from a few minutes to possibly a couple of hours in order to stabilize cardiac hemodynamics, increase perfusion, reduce refractoriness dispersion inhibiting the development of re-entry circuits, and thus prevent the VTA from developing. Block 23 needs access to the R-R interval information along with access to the ventricular electrodes for pacing and sensing purposes.

In a future drug therapy implantable device, instead of the pacing therapy indicated in the previous paragraph, a preventive drug therapy can also be initiated.

An alternative or addition to the preventive pacing is for 22 to cause 23 to notify the patient through the Mini Speaker, 25, or the Vibrator circuit, 26, or notify a service center by sending the warning in the form of a radio-frequency signal through the Antenna 27 to possibly an external retransmitter worn by the patient, which can access cellular phone circuits. Such auditory tone or vibration or RF signals have been used in existing implantable devices to notify the patient of conditions like low battery, broken lead and unusual arrhythmic conditions, either directly, when using Mini Speaker 25 and Vibrator 26, or indirectly by means of the Antenna 27.

In addition to the preventive therapy, the preventive implantable device can also offer a programmable delayed anti-tachyarrhythmic therapy mode. If no Vagal Fatigue Warning has been issued in a prior programmed time interval, for example 3 hours, and then an episode of VTA is detected, 22 may cause the programmed anti-tachyarrhythmic therapy which is managed by block 23 to be delayed by a programmable time, for example 2 seconds. At the end of this delay, the implantable device will make its standard verification of VTA status prior to delivery of therapy. If the verification, which typically consists of comparing the R-R interval with the VTA limits, indicates that the VTA is still on, then anti-tachyarrhythmic therapy is initiated. Else therapy is aborted, as it would be if the VTA were to break after detection but prior to therapy delivery.

As an alternative, instead of delaying anti-tachyarrhythmic therapy, 22 may cause the next VTA detection which is managed by block 23 to be altered in such a way that a longer VTA detection time is required. Without the Vagal Fatigue Warning, there would be no basis for delaying any detection.

Figure 2:
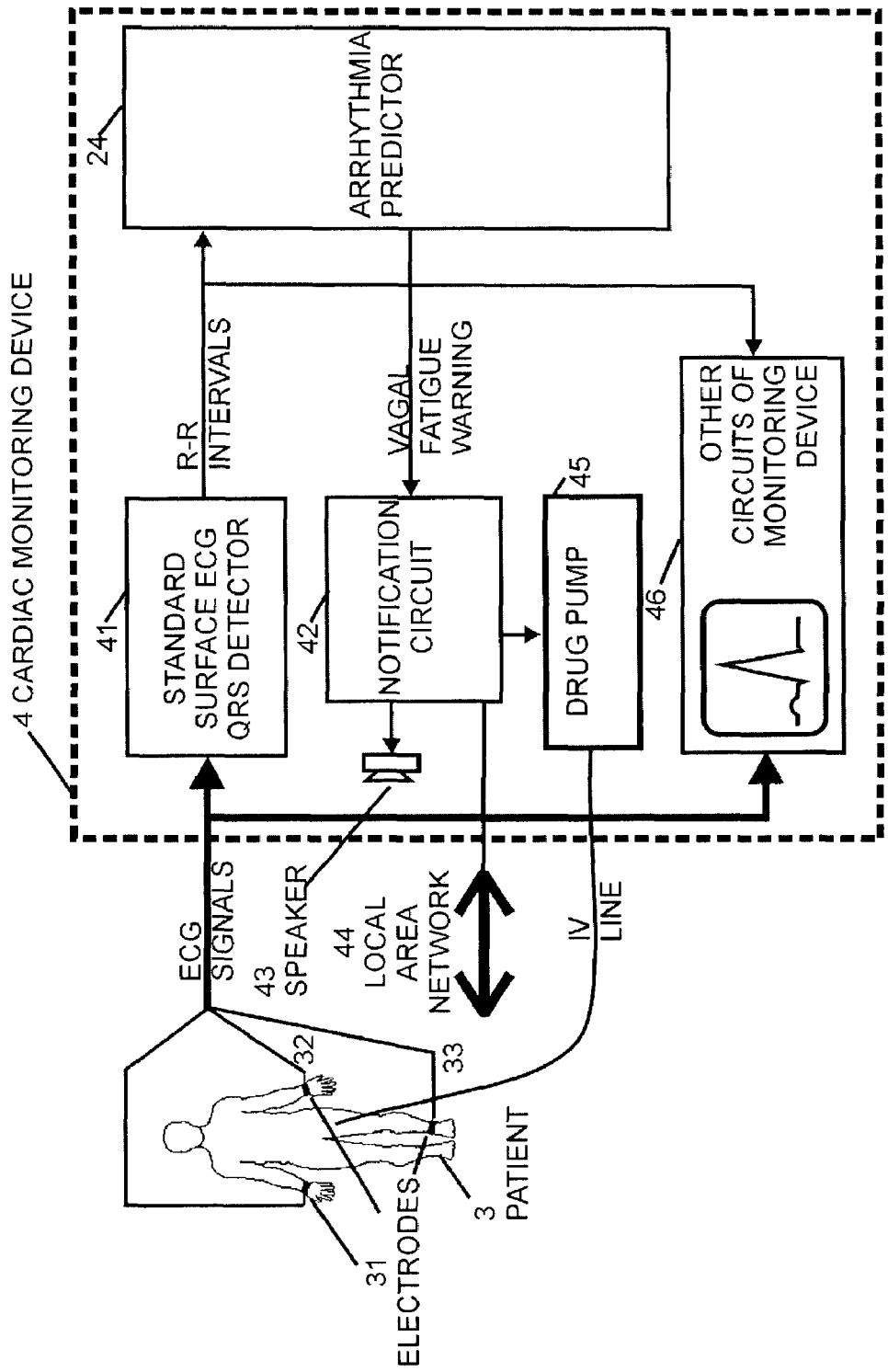
FIG. 2. is a functional schematic diagram of a notification and preventive external cardiac monitoring device according to a preferred embodiment of the present invention.

In FIG. 2, a preferred embodiment in the case of an external cardiac monitoring device is illustrated. Since this invention is about the use of R-R intervals to predict an imminent episode of VTA, and the actions to be taken as a result of this prediction, the vehicles for implementing the invention outside a human body are many. Any device that can measure the heart rate or the R-R interval on a beat by beat basis can be modified to use this invention to add a VTA prediction capability. For purpose of illustration, a modified electrocardiogram (ECG) monitor is described here. Items 31 through 33, 41, and 46 are specific to a standard ECG monitor and are described here only for illustration purposes. Similar blocks for different types of devices can be derived by a person skilled in the art of external cardiac devices.

The surface ECG signals are collected from the Patient, 3. The generic locations of the electrodes 31 through 33 are shown. More than 3 electrodes can also be used to generate complex ECG for reasons outside the scope of this invention, for example for analysis by a cardiologist. Often the electrodes are positioned on the chest of the patient, instead of the limbs.

The Cardiac Monitoring Device 4 is functionally similar to the Implantable Device 2 of FIG. 1. The surface ECG signals are processed by the Standard Surface ECG QRS Detector 41. Functionally, this is similar to 21 in FIG. 1, with the difference being that this works on surface ECG signals. As mentioned earlier, any standard hardware within the cardiac monitoring industry can be used to collect the R-R intervals. This invention is about processing the R-R intervals to predict an imminent episode of VTA and the actions to be taken when such a prediction has been made.

The R-R intervals which are produced by 41 are processed by the Arrhythmia Predictor, 24, of the present invention which is functionally identical to the Arrhythmia Predictor 24 in FIG. 1. Since this is an external device, the Notification Circuit 42 is used to notify the patient, or the nurse, when a Vagal Fatigue Warning is raised about an imminent episode of VTA. The notification can be in an auditory form, for example by means of the Speaker 43, or an electrical signal is sent via the Local Area Network 44 to the nurse's station. This will prompt the nurse to take therapeutic actions, such as increasing the amount of anti-arrhythmic drug. In the case the cardiac monitoring device has a built-in Drug Pump 45, 42 would send a command to 45 to deliver either an increased dosage of anti-arrhythmic drug, or to start delivering such a drug through an intravenous (IV) line. Alternatively, 42 can signal, by means of the link 44, an external drug delivery system to increase the dosage of anti-arrhythmic drug. If it were not for the advance warning of vagal fatigue provided by the present invention, it would not be known, in advance of a serious cardiac problem, that any of the therapy options listed above should be provided.

The Other Circuits of the Monitoring Device 46 needs the ECG signals and the R-R intervals to perform other diagnostic functions along with a display of waveforms.

Figure 3:
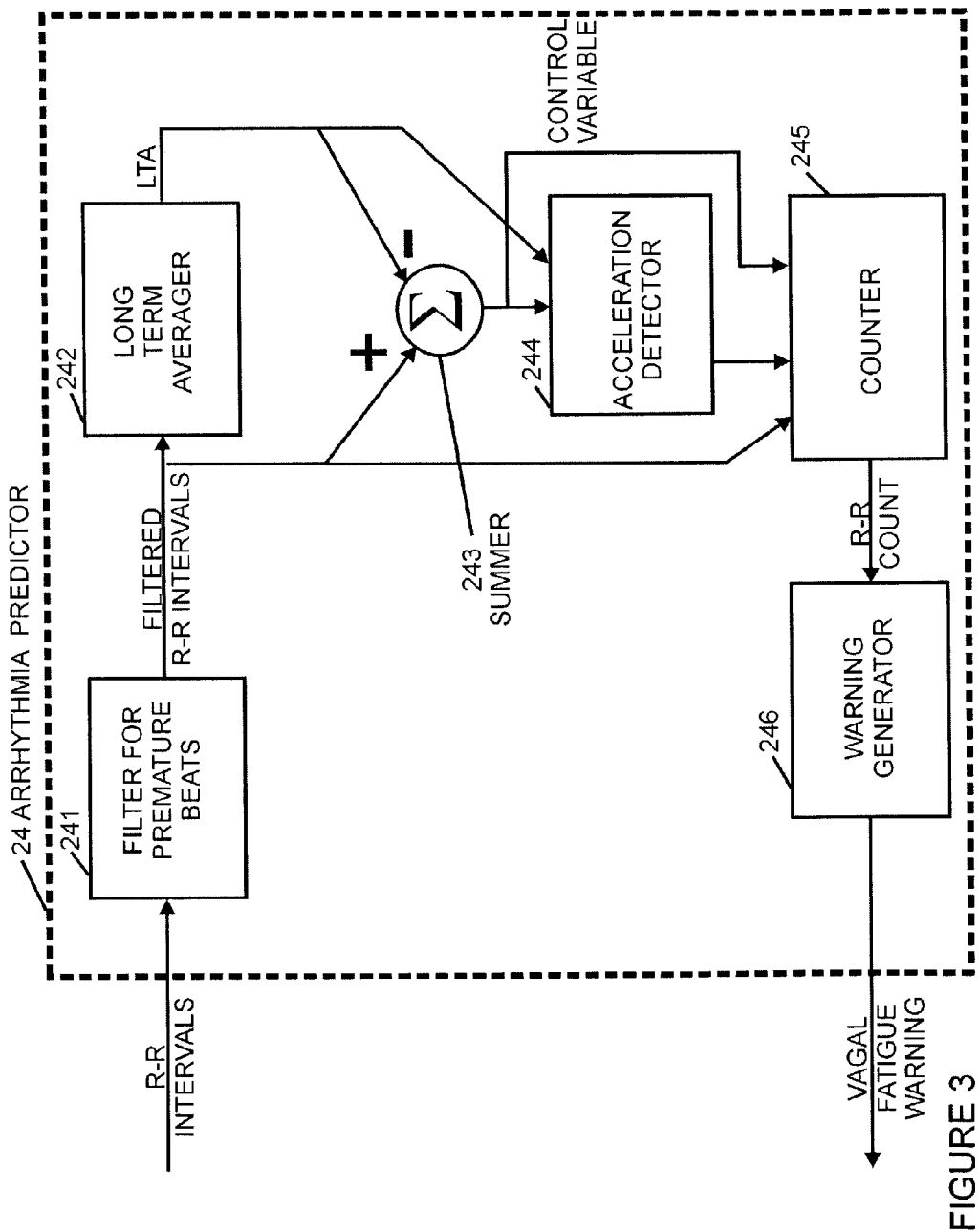
FIG. 3 is the block diagram for the Arrhythmia Predictor in a preferred embodiment of the present invention.

In FIG. 3 the R-R intervals are processed by 24 to generate the Vagal Fatigue Warning. The R-R intervals come to the input of the Filter for Premature Beats 241. A digital filter is used to remove premature beats and the following compensating beat to generate Filtered R-R Intervals which form the general heart interval trend line. For example, during a steady rhythm with R-R intervals of 900 ms, a premature beat may take one of the following forms: 900, . . . , 900, 400, 500, 900; 900, . . . , 900, 600, 1200, 900. In the preferred embodiment, a non-linear median filter, as can be found in most textbooks on image processing or non-linear digital filters, is used. The premature beat and the following beat are replaced by two intervals of 900 ms. A digital lowpass filter can also be used, where these two beats may be replaced by intervals with some average values of the previous beats, for example 800 ms.

Once the premature beats are filtered as per above, the LTA (Long Term Average) is computed in 242. The Long Term Averager 242 can be implemented by calculating a moving average over a period of 20 to 30 seconds. Another implementation, which is the preferred embodiment of the present invention, is to use exponential averaging.

$$avg(n)=0.05*RR(n)+0.95*avg(n-1)$$

where avg(n) is the LTA sample at time n, RR(n) is the current Filtered R-R Interval, and avg(n−1) is the previous LTA sample. The factors of 0.05 and 0.95 have to add to 1, but can be chosen pretty arbitrarily. The applicant of the present invention determined the factors 0.05 and 0.95 to yield the best overall results from extensive analysis of R-R interval history recorded prior to episodes of VTA. In practical implementations, these values should be programmable by the physician based on his/her experience and the special conditions of the patient.

The output of the Summer 243 is the Control Variable. This is the difference between the Filtered R-R Intervals and the LTA. The Control Variable is negative when the Filtered R-R interval is shorter than the LTA.

In the Acceleration Detector 244, only Control Variables with negative values are considered. These correspond to episodes of heart rate acceleration. Whenever the magnitude of the Control Variable is larger than a threshold, typically set as 4% of the LTA, an acceleration flag is raised for that Filtered R-R Interval. The 4% value was found to be overall optimal from extensive analyses performed by the inventor. This acceleration flag is the output of the Acceleration Detector 244. 244 only acts upon acceleration during times when the Filtered R-R Intervals remain within the normal sinus zone, for example longer than 500 ms, corresponding to 120 beats per minute.

The Counter 245 starts counting the number of R-R intervals when the acceleration flag is first set. An alternative to counting intervals is to measure the time. The preferred approach of this invention is to count the number of R-R intervals. The count is cleared whenever the Control Variable output from the Summer 243 becomes either positive or zero, indicating that the heart rhythm acceleration has ended. At any time during the count, if the Filtered R-R Interval becomes shorter than a programmed limit, typically called the Tachycardia Limit, or an even shorter programmed limit, the Fibrillation Limit, a programmed number of times, e.g. 3, over a programmed window of, for example but not limited to, 8 R-R intervals, the count is cleared, since the patient has entered a VTA and prediction is no longer meaningful. In summary once started, by the output of 244, the R-R count increases until either the Control Variable, from 243, becomes zero or positive, or the patient has entered a VTA, as indicated by the output of 241, under which conditions it resets.

The Warning Generator 246 generates the Vagal Fatigue Warning when the R-R count exceeds a programmed value, for example 60 R-R intervals, or a programmed number of time units equivalent to, for example, 30 seconds.

Figure 4A:
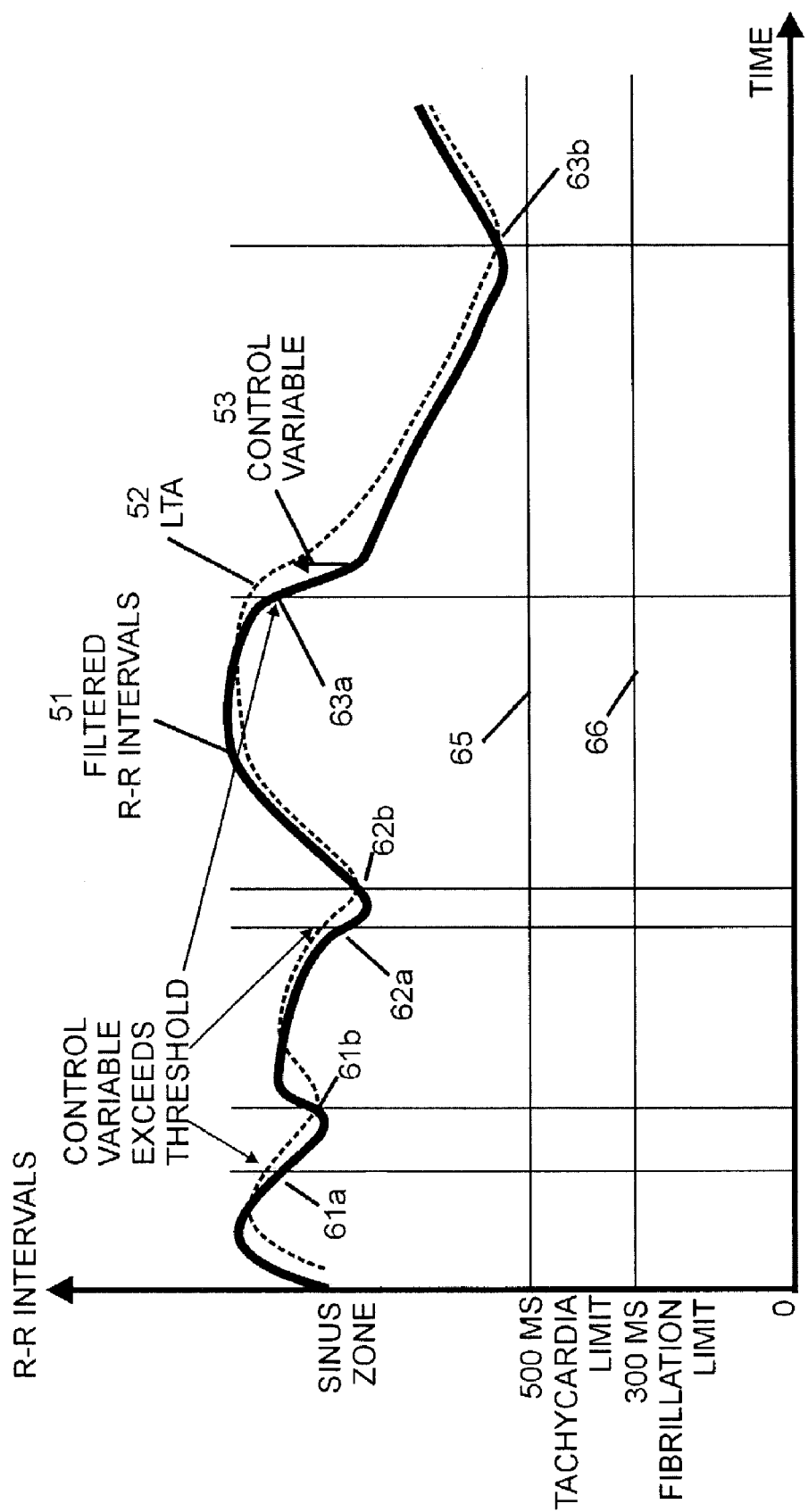
FIG. 4A is a graph illustrating the relationship between the key waveforms and variables of a preferred embodiment of the present invention.

In FIG. 4a the key signals of the Arrhythmia Predictor 24, of FIG. 3, are illustrated. The prediction is performed on Filtered R-R Intervals in the sinus zone, with intervals longer than the Tachycardia (detection) Limit 65, shown in FIG. 4a as 500 ms, and the Fibrillation (detection) Limit 66, shown in FIG. 4a as 300 ms. These two detection limits are used by devices, such as an ICD, in the detection of the different types of VTAs, namely ventricular tachycardia and ventricular fibrillation, and in the selection of the therapies. The curve 51 represents the Filtered R-R Intervals output of the filter 241 of FIG. 3. The curve LTA 52, the output of the Long Term Averager 242 of FIG. 3, lags behind the curve 51. The Control Variable 53, the output of the Summer 243 in FIG. 3, is the difference signal between the curves 51 and 52. It is positive in the direction of the arrow shown in FIG. 4a. At the times 61a, 62a and 63a, the Control Variable 53 exceeds in the negative direction the threshold, which is set for, example, at 4% of the LTA. At the times 61b, 62b and 63b, the Control Variable is zero as the curves 51 and 52 crosses one another.

Figure 4B:
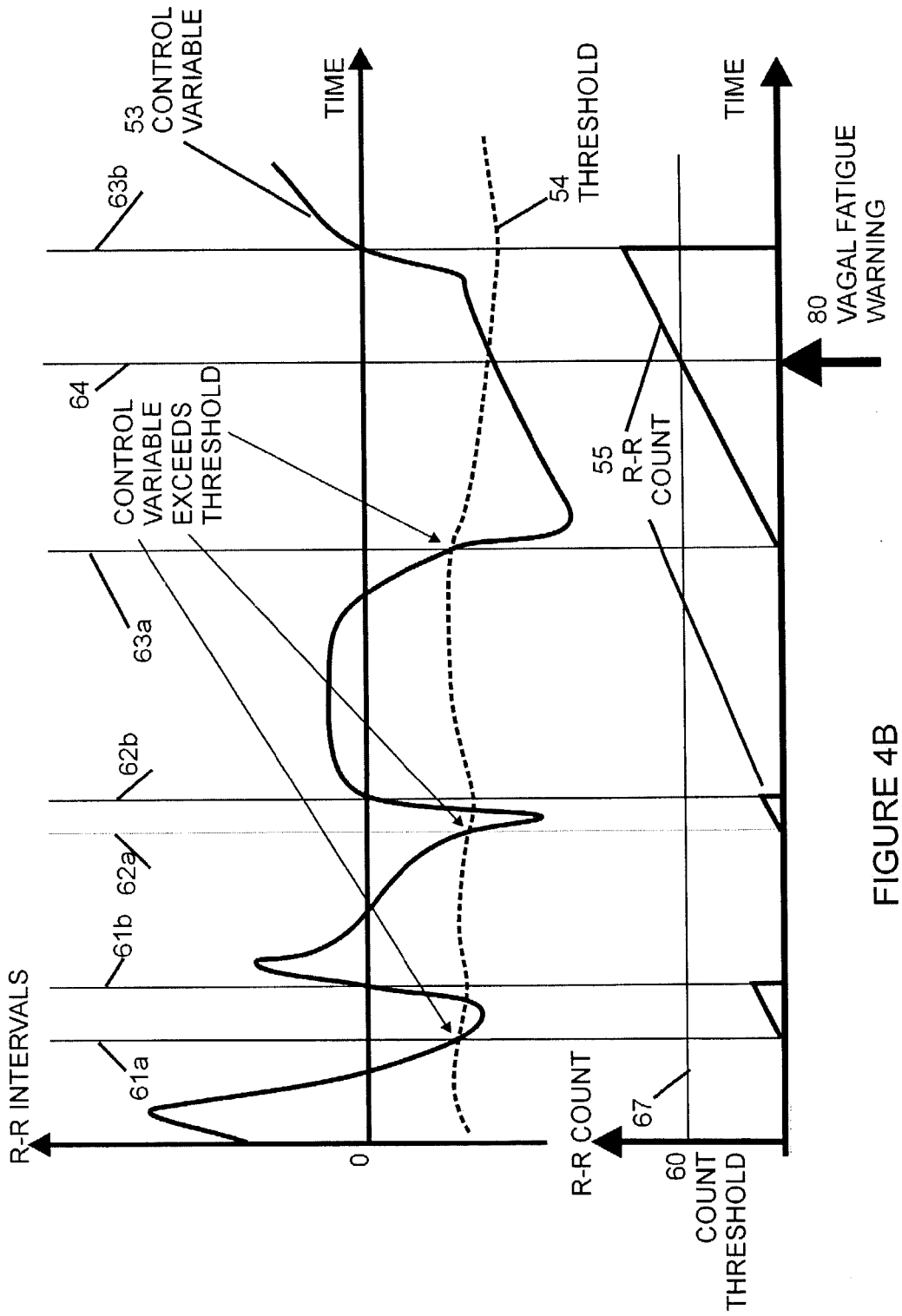
FIG. 4B is a graph illustrating the detailed timings of a preferred embodiment of the present invention.

In FIG. 4b, the Control Variable 53 is plotted. Since only negative values of the control variable, which corresponds to a rhythm acceleration, are considered, the part of interest in the plot is below the Time axis. The Threshold 54 is equal to 4% of the LTA. At times 61a, 62a, and 63a the Control Variable curve 53 crosses the Threshold curve 54. At times 61b, 62b, and 63b the Control Variable curve 53 crosses the Time axis. The R-R Count 55, counting the number of R-R intervals in the preferred embodiment, is started whenever the Control Variable curve 53 crosses the Threshold curve 54 in the negative direction. The R-R Count is reset when curve 53 crosses the Time axis, i.e. when the Control Variable is zero. Thus, curve 55 has non zero values between the time intervals (61a, 61b), (62a, 62b) and (63a, 63b).

In FIG. 4b, the Count Threshold 67 is set at 60 R-R intervals. Since the durations from 61a to 61b, and from 62a to 62b are less than the Count Threshold, no vagal fatigue is declared. The negative run of the Control Variable 53 that started at time 63a exceeds the Count Threshold 67 at time 64, resulting in the Vagal Fatigue Warning of Imminent Tachyarrhythmia 80 being issued.

Figure 5:
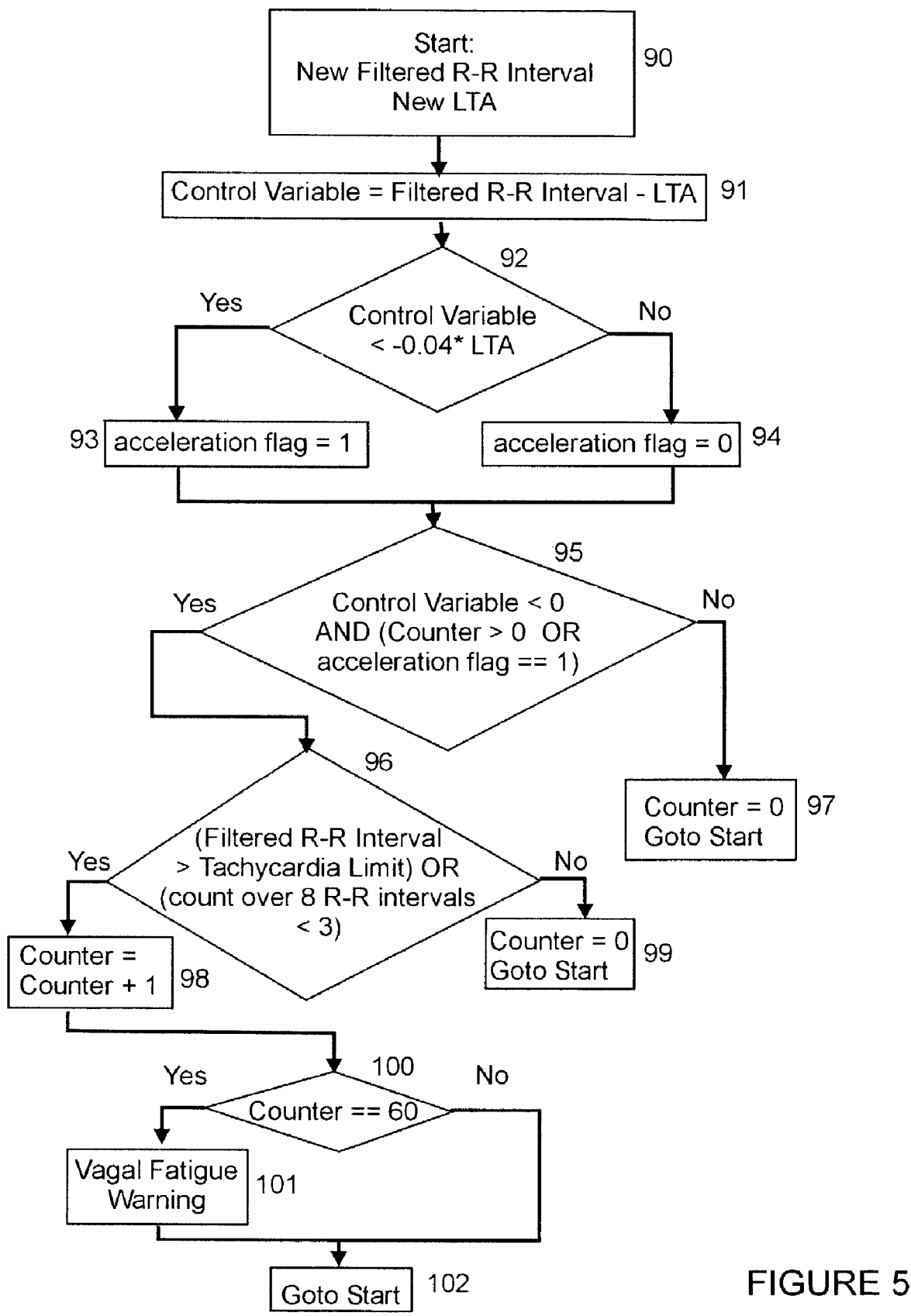
FIG. 5 is the flow diagram for the VTA prediction algorithm. This is a summary of FIGS. 4a and 4b.

In FIG. 5, a flow diagram of the Vagal Fatigue prediction method of the present invention is presented. It is a summary of FIGS. 4a and 4b. Each time a new R-R interval is available, a new Filtered R-R Interval and a new LTA is computed in block 90. The Control Variable is computed in block 91. In block 92, the Control Variable is compared with, for example, 4% of the LTA. If the Control Variable is negative and less than, for example, 4% of the LTA, the acceleration flag is set to 1 in block 93. Else it is set to 0 in block 94. When, in block 95, the Control Variable is negative, i.e. a heart rhythm acceleration faster than 96% of the LTA (100%−4%=96%), and this is in the middle of a run of negative Control Variables, as indicated by a positive Counter, or the acceleration flag is 1, then tentatively this is an acceleration interval. The reason for testing for Counter>0 first is because this is typically the more frequently met test, for negative Control Variable. Else there is no acceleration and the Counter is set to 0, and go back to wait for the next R-R interval at Start. In block 96, the Filtered R-R interval is checked for being faster than the Tachycardia Limit. If this is not a tachycardia interval, i.e. the R-R interval is greater than the Tachycardia Limit, then proceed to increment the Counter in block 98. If this is a tachycardia interval, i.e. the Filtered R-R interval is less than the Tachycardia Limit, and over the past, for example, 8 R-R intervals there has been less than 3 such intervals, proceed to block 98 to increment the Counter. The purpose of allowing up to 3 fast R-R intervals is to ignore a run of premature complexes that could not be completely removed by the Filter 241 in FIG. 3. Else the rhythm is already in tachycardia or fibrillation. Then clear the counter and go back to Start. Note that through the use of the test Counter>0 in block 95, once the threshold has been met, the counter will count until the Control Variable becomes 0 or positive. In block 100, if the Counter is equal to a programmable count, for example 60, a Vagal Fatigue Warning is generated in block 101. Else go back to Start and wait for the next R-R interval.

An alternative to the test in block 92, which should be obvious to one skilled in the art, is to test for the condition that the Filtered R-R Interval is less than 96% of the LTA.

What is claimed is:

1. A method for predicting an imminent tachyarrhythmia that detects a prolonged heart rhythm acceleration, even if and when the heart is driven at normal sinus rates;

applies a filter on the heart beat interval data to remove the effects of premature beats;

computes the long term average of heart beat intervals based on the filtered heart beat intervals; and uses the difference signal between the filtered heart beat intervals and the long term average of heart beat intervals to predict imminent tachyarrhythmia.

2. The method of claim 1 that compares the difference signal between the filtered heart beat intervals and the long term average of heart beat intervals to a programmable percentage of the long term average of heart beat intervals to determine a heart rhythm acceleration, upon such a heart rhythm acceleration, counts the number of heart beats until the difference signal returns to zero or changes sign, and upon the count exceeding a programmable number, causes a signal which signified imminent ventricular tachyarrhythmia to be issued.

3. The method of claim 1 that compares the difference signal between the filtered heart beat intervals and the long term average of heart beat intervals to a programmable percentage of the long term average of heart beat intervals to determine a heart rhythm acceleration, upon such a heart rhythm acceleration, tracks the amount of time until the difference signal returns to zero or changes sign, and upon the amount of time exceeding a programmable value, causes a signal which signified imminent ventricular tachyarrhythmia to be issued.

4. A cardiac device, which comprises the method of claim 1 or 2 or 3, which can generate a signal which signifies imminent tachyarrhythmia.

5. The device of claim 4 which is an implantable cardioverter defibrillator.

6. The implantable defibrillator of claim 5 which generates a signal which can be perceived by the patient as notification of imminent tachyarrhythmia.

7. The implantable cardioverter defibrillator of claim 6 which can initiate preventive therapy upon a signal which signifies imminent tachyarrhythmia.

8. The implantable cardioverter defibrillator of claim 7, which delays anti tachyarrhythmic therapy for a programmable time duration, when no signal indicating imminent tachyarrhythmia has been generated within a previous specified time period, and a tachyarrhythmia has been detected.

9. The device of claim 4, which is a pacemaker.

10. The pacemaker of claim 9 which generates a signal which can be perceived by the patient as notification of imminent tachyarrhythmia.

11. The pacemaker of claim 10, which can initiate preventive therapy upon a signal which signifies imminent tachyarrhythmia.

12. The device of claim 4, which is an implantable drug delivery system and which can deliver a preventive drug therapy upon a signal which signifies imminent tachyarrhythmia.

13. The device of claim 4, which is an external cardiac monitor.

14. The cardiac monitor of claim 13 that can convert the signal that signifies imminent tachyarrhythmia to an audible signal.

15. The cardiac monitor of claim 14 that can convert the signal that signifies imminent tachyarrhythmia into an electronic notification to be sent out over a network.

16. The cardiac monitor of claim 15 that can initiate preventive drug therapy through a drug delivery subsystem upon the signal that signifies imminent tachyarrhythmia.

17. The cardiac monitor of claim 15 that can initiate preventive drug therapy through an external device.

18. The implantable cardioverter defibrillator of claim 6, which delays anti tachyarrhythmic therapy for a programmable time duration, when no signal indicating imminent tachyarrhythmia has been generated within a previous specified time period, and a tachyarrhythmia has been detected.

19. The implantable cardioverter defibrillator of claim 5 which can initiate preventive therapy upon a signal which signifies imminent tachyarrhythmia.

20. The implantable card ioverter defibrillator of claim 19, which delays anti tachyarrhythmic therapy for a programmable time duration, when no signal indicating imminent tachyarrhythmia has been generated within a previous specified time period, and a tachyarrhythmia has been detected.

21. The pacemaker of claim 9, which can initiate preventive therapy upon a signal which signifies imminent tachyarrhythmia.

22. The cardiac monitor of claim 13 that can convert the signal that signifies imminent tachyarrhythmia into an electronic notification to be sent out over a network.

23. The cardiac monitor of claim 22 that can initiate preventive drug therapy through a drug delivery subsystem upon the signal that signifies imminent tachyarrhythmia.

24. The cardiac monitor of claim 22 that can initiate preventive drug therapy through an external device.

\* \* \* \* \*